United States Patent [19]

Nitta et al.

[11] 4,440,689

[45] Apr. 3, 1984

[54] ACYLOXYSTEROIDS AND PROCESS FOR PRODUCING SAME

[75] Inventors: Issei Nitta, Machida; Shinichiro Fujimori, Yokohama; Toshio Haruyama, Sagamihara; Shinya Inoue, Yamato, all of Japan

[73] Assignee: Mitsubishi Chemical Industries, Limited, Tokyo, Japan

[21] Appl. No.: 396,447

[22] Filed: Jul. 8, 1982

[30] Foreign Application Priority Data

| Jul. 22, 1981 | [JP] | Japan | 56-114867 |
|---|---|---|---|
| Jul. 22, 1981 | [JP] | Japan | 56-114868 |
| Jul. 23, 1981 | [JP] | Japan | 56-115691 |
| Jul. 28, 1981 | [JP] | Japan | 56-118340 |
| Jul. 28, 1981 | [JP] | Japan | 56-118341 |
| Jul. 28, 1981 | [JP] | Japan | 56-118342 |
| Jul. 28, 1981 | [JP] | Japan | 56-118344 |
| Jul. 29, 1981 | [JP] | Japan | 56-118710 |
| Aug. 26, 1981 | [JP] | Japan | 56-133843 |
| Aug. 27, 1981 | [JP] | Japan | 56-134768 |

[51] Int. Cl.$^3$ ............................................. C07J 9/00
[52] U.S. Cl. .......................... 260/397.4; 260/397.45; 260/397.47
[58] Field of Search ........... 260/397.4, 397.45, 397.47; /Steroids MS File

[56] References Cited

U.S. PATENT DOCUMENTS 3,992,422  11/1976  Green ........................... 260/397.45
4,113,680   9/1978  Kamano et al. ............... 260/397.45

Primary Examiner—Elbert L. Roberts
Attorney, Agent, or Firm—Oblon, Fisher, Spivak, McClelland & Maier

[57] ABSTRACT

There is disclosed novel intermediates, i.e. acyloxysteroids, which are useful for the preparation of corticoids such as hydrocortisone and prednisolone, and a process for producing the same.

10 Claims, No Drawings

ACYLOXYSTEROIDS AND PROCESS FOR PRODUCING SAME

BACKGROUND OF THE INVENTION

1. Field of the Invention

This invention relates to acyloxysteroids which are useful as a novel intermediate for use in the preparation of adrenocortical hormones such as hydrocortisone, prednisolone and the like.

2. Description of the Prior Art

Recently, androst-4-ene-3,17-dione and androsta-1,4-diene-3,17-dione have been produced in large quantities and inexpensively from sterols such as cholesterol, sitosterol and the like by the use of microorganisms belonging to the genus Mycobacterium and thus various steroidal drugs such as estrone, testosterone, spironolactone, etc. have been produced from these starting materials.

On the other hand, adrenocortical hormones (corticoids) which occupy a major proportion of the steroidal drugs are still prepared using as an intermediate progesterone from stigmasterol or 16-dehydropregnenolone from diosgenin, or they are prepared from bile acids via a process comprising many steps.

We have made extensive studies to develop a more economical process for preparing corticoids from starting materials including not only the aforementioned androst-4-ene-3,17-dione and androsta-1,4-diene-3,17-dione which have recently been produced in large quantities and inexpensively, but also androsta-4,9(11)-diene-3,17-dione which has been produced from 9α-hydroxyandrost-4-ene-3,17-dione which has also recently been produced by a fermentative process. It has now been found that acyloxysteroids which are useful as a starting material in the preparation of corticoids can be obtained from the above-described starting materials.

SUMMARY OF THE INVENTION

The present invention relates to novel intermediates, i.e., acyloxysteroids such as, e.g., 21,21-diiodo-17α-hydroxypregna-1,4-diene-3,20-dione 17-acetate, 21-iodo-17α-hydroxypregna-1,4-diene-3,20-dione 17-acetate, 21,21-dibromo-17α-hydroxypregn-4-ene-3,20-dione 17-acetate, 21-bromo-17α-hydroxypregn-4-ene-3,20-dione 17-acetate, etc., which are useful for the preparation of corticoids such as hydrocortisone and prednisolone, and a process for producing the same.

DESCRIPTION OF THE PREFERRED EMBODIMENTS

The acyloxysteroids according to the present invention are represented by the following general formula (I):

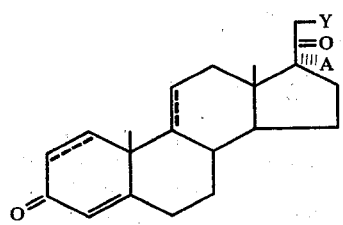

(I)

wherein the dotted lines on the ring represent a single or double bond, A represents an acyloxy group, and Y represents Br, Br₂, I or I₂.

The preparation of the above compounds according to the invention is then described.

(A) When the compound of the general formula (I) is a diiodosteroid of the general formula (Ia):

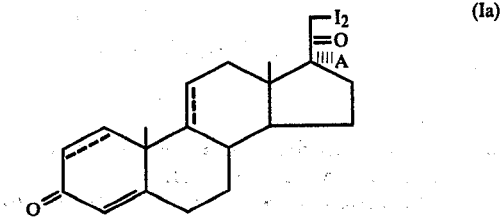

wherein the dotted lines and A are as defined in the general formula (I), it can be prepared through a procedure represented by the following reaction schema:

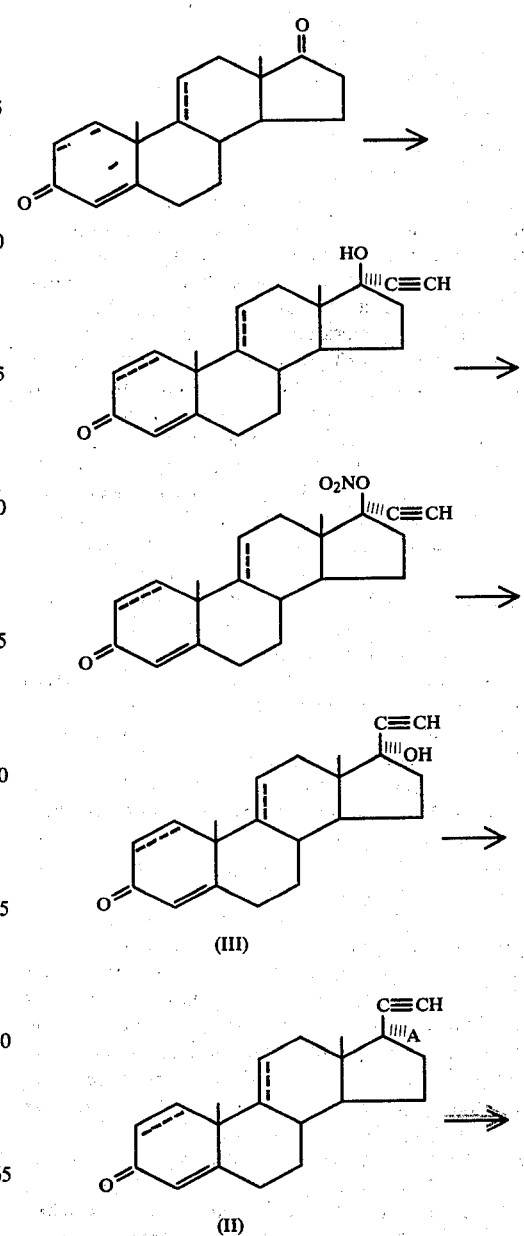

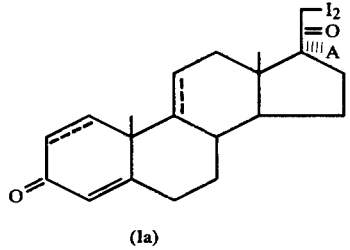

(Ia)

In the above formulae, the dotted lines and A are as defined in the general formula (I).

The diiodosteroid can be prepared by reacting an iodizing agent capable of releasing positive iodine atom with a 17β-ethynyl-17α-acyloxysteroid of the general formula (II):

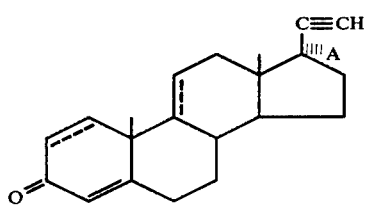

wherein the dotted lines on the ring represent a single or double bond, and A represents an acyloxy group. For instance, when either iodizing agents capable of generating positive iodine atom such as N-iodosuccinimide, N-iodoacetamide and the like, or positive iodine atom which have been generated in the reaction system by oxidation of iodine with peracids such as peracetic acid or metal ions having the ability of oxidation potential such as cupric acetate is reacted with steroids such as 17β-ethynyl-17α-hydroxyandrosta-1,4-dien-3-one 17-acetate, 17β-ethynyl-17α-hydroxyandrost-4-en-3-one 17-acetate, 17β-ethynyl-17α-hydroxyandrosta-4,9(11)-dien-3-one 17-acetate and the like, these starting steroids are converted into 21,21-diiodo-17α-hydroxypregna-1,4-diene-3,20-dione 17-acetate, 21,21-diiodo-17α-hydroxypregn-4-ene-3,20-dione 17-acetate, 21,21-diiodo-17α-hydroxypregna-4,9(11)-diene-3,20-dione 17-acetate and the like, respectively.

The preparation method is described in more detail. The iodizing agent capable of releasing positive iodine atom usable for this purpose includes N-iodoimides and N-iodoamides such as N-iodosuccinimide N-iodoacetamide and the like. Furthermore, the positive iodine atom can be generated in the reaction system by reacting various oxidizing agents with iodine. In the latter case, examples of the oxidizing agents include peracids such as peracetic acid, perbenzoic acid and the like, hydroperoxides such as hydrogen peroxide, t-butyl hydroperoxide and the like, salts of metallic ions having the oxidization potential such as silver nitrate, cupric nitrate, cupric acetate and the like. Among them, peracetic acid is the most preferred oxidizing agent because of its inexpensiveness, industrial availability, and good reactivity. The amount of the iodizing agent is generally two or more equivalents, preferably 2.05-2.5 equivalents, of the acetylene compound used.

The solvents may be any solvents ordinarily employed from the industrial aspect but methyl ketones such as acetone, methyl ethyl ketone and the like which react with the iodizing agents are not favorable. Preferred solvents are aliphatic acids such as acetic acid, propionic acid and the like.

In the reaction procedure, it is the usual practice to allow water to coexist with reaction solvents. If water is absent, water is added after completion of the reaction in order to hydrolyze the resulting product to obtain a desired diiodo ketone. Water is generally used at least in an equimolar amount with respect to the acetylene compound and is suitably in an amount of 5 to 20% of the solvent used.

The acyloxysteroids of the general formula (II) which are employed as the starting material in accordance with the process of the invention can be prepared by reacting carboxylic anhydrides or acid halides with 17β-ethynyl-17α-hydroxysteroids of the general formula (III):

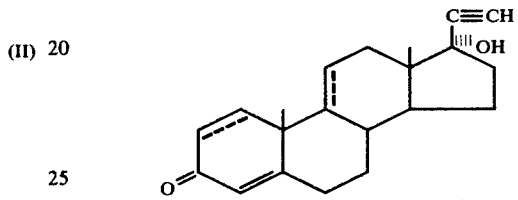

wherein the dotted lines on the ring independently represent a single or double bond.

This preparation is feasible by several procedures.

The first procedure includes the reaction of a carboxylic anhydride such as acetic anhydride with the 17β-ethynyl-17α-hydroxysteroid of the general formula (III) in an aromatic amine such as pyridine. In the case, the acid anhydride should be used in an amount of equimole or more, preferably five or more times in mole as great as the steroid. The reaction temperature is in the range of 80° to 150° C., preferably 100° to 135° C.

The second procedure comprises the reaction of the steroids of the general formula (III) with a carboxylic anhydride in a solvent such as acetic acid.

In this case, acid compounds or Lewis acids such as p-toluenesulfonic acid, trifluoroacetic acid, sulfuric acid, phosphoric acid, zinc chloride, iron chloride and the like are used as a catalyst. The reaction temperature is normally in the range of 0° to 50° C.

(B) Preparation of compounds of the invention in case where the compounds of the general formula (I) are monoiodosteroids of the general formula (Ib):

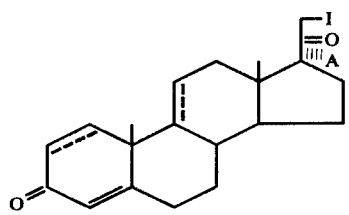

wherein the dotted lines and A are as defined in the general formula (I).

The monoiodosteroids represented by the general formula (Ib) according to the invention include, for example, 21-iodo-17α-hydroxypregn-4-ene-3,20-dione 17-acetate, 21-iodo-17α-hydroxypregn-4-ene-3,20-dione 17-propionate, 21-iodo-17α-hydroxypregna-1,4-diene-3,20-dione 17-acetate, 21-iodo-17α-hydroxypregna-4,9(11)-diene-3,20-dione 17-acetate and the like.

In order to prepare the monoiodosteroid of the general formula (Ib) it is sufficient to contact the diiodosteroid of the general formula (Ia) with hydrogen atom-containing organic solvents.

The diiodosteroids of the general formula (Ia) include, for example, 21,21-diiodo-17α-hydroxypregn-4-ene-3,20-dione 17-acetate, 21,21-diiodo-17α-hydroxypregn-4-ene-3,20-dione 17-propionate, 21,21-diiodo-17α-hydroxypregna-1,4-diene-3,20-dione 17-acetate, 21,21-diiodo-17α-hydroxypregna-4,9$^{(11)}$-diene-3,20-dione 17-acetate and the like.

The hydrogen atom-containing organic solvents used for the above purpose are organic solvents which are capable of releasing hydrogen ions (protons) or hydrogen radicals and are almost all the ordinarily, industrially employed solvents such as acetic acid, triethylamine, dimethylformamide, acetonitrile, ethyl acetate, acetone, tetrahydrofuran, methanol, chloroform, benzene and the like. Preferred solvents are amines such as triethylamine, diethylamine and the like, and methyl ketones such as acetone, methyl ethyl ketone and the like, among which the latter methyl ketones are most preferred.

These solvents are used in amounts enough for ordinary use as solvent.

When methyl ketones are used, the coexistence of at least one member selected from basic compounds including alkali metal hydroxides such as sodium hydroxide, potassium hydroxide and the like, aliphatic amines such as triethylamine, diethylamine and the like, and aromatic amines such as dimethylaminoaniline, pyridine, and carbonates and carboxylates of the basic compounds such as potassium carbonate, potassium acetate, triethylamine acetate and the like will give an extremely promoting effect of the reaction thus improving the yield of monoiodo ketones (Ib) to a remarkable extent.

The basic compounds or carbonates or carboxylates thereof are generally used in equimolar or greater amounts relative to the diiodosteroids (Ia). The reaction temperature is generally in the range of −10° to 100° C.

Moreover, the monoiodosteroids of the general formula (Ib) can be prepared by reducing the diiodosteroids of the general formula (Ia) with dithionites.

The dithionites used in the practice of the invention include sodium dithionite (hydrosulfite), potassium dithionite, calcium dithionite, zinc dithionite, lithium dithionite, magnesium dithionite and the like, among which sodium dithionite is favorably used. The amount is generally in the range of 1.0 to 1.3 equivalents, preferably 1.0 to 1.2 equivalents, with respect to the α,α-diiodo ketone. Greater amounts are disadvantageous in that monoiodo ketones are further reduced to ketones and thus a desired yield cannot be obtained.

The solvents used may be any industrially employed solvents such as benzene, tetrahydrofuran, acetone, acetic acid and the like. The reaction temperature is in the range of 0° to 50° C., preferably 5° to 30° C.

According to this procedure, the monoiodosteroid can be obtaied by directly adding dithionites to the reaction solution for the production of a corresponding diiodosteroid without isolating the diiodosteroid from the reaction solution.

For instance, an ethynylated steroid of the general formula (II):

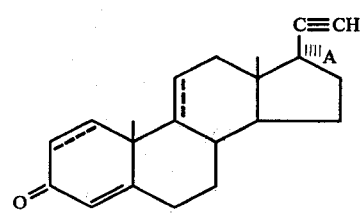

wherein the dotted lines and A are as defined in the general formula (I), is reacted with positive iodine atom to obtain a solution of the diiodosteroid of the general formula (Ia), to which solution is directly added a dithionite to give the monoiodosteroid of the general formula (Ib).

(C) Preparation of compounds of the invention in case where the compounds of the general formula (I) are dibromosteroids of the general formula (Ic):

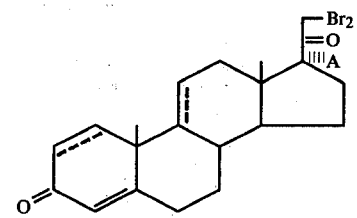

wherein the dotted lines and A are as defined in the general formula (I).

Compounds of the general formula (Ic) include, for example, 21,21-dibromo-17α-hydroxypregn-4-ene-3,20-dione 17-acetate, 21,21-dibromo-17α-hydroxypregn-4-ene-3,20-dione 17-propionate, 21,21-dibromo-17α-hydroxypregna-1,4-diene-3,20-dione 17-acetate, 21,21-dibromo-17α-hydroxypregna-4,9$^{(11)}$-diene-3,20-dione 17-acetate and the like.

The dibromosteroids of the general formula (Ic) can be prepared by causing halogenating agents capable of releasing positive bromine atom to react with the 17β-ethynyl-17α-acyloxysteroid of the general formula (II):

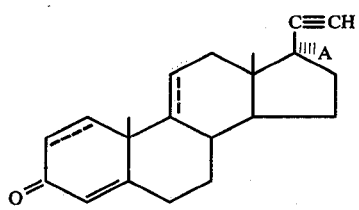

wherein the dotted lines and A are as defined in the general formula (I).

In order to produce the dibromosteroids of the general formula (Ic) by reacting halogenating agents capable of releasing positive bromine atom with the 17β-ethynyl-17α-acyloxysteroids of the general formula (II) as mentioned above, there are used, as the halogenating agent, N-bromoimides and N-bromoamides such as N-bromosuccinimide, N-dibromodimethylhydantoin, N-dibromobenzenesulfonamide, N-bromoacetamide and the like. The amount is in the range of 2 times or more in mole, preferably 2.1 to 3 times in mole, that of 17β-ethynyl-17α-acyloxysteroid. The reaction solvents are usually mixed solvents of aliphatic carboxylic acids such as acetic acid, propionic acid, butyric acid and the like, and water. The reaction temperature is in the range of −5° to 60° C., preferably 0° to 30° C. For the purpose of neutralizing hydrobromic acid produced by side reaction, there may be added alkali metal salts of carboxylic acids such as sodium acetate, potassium propionate and the like.

(D) Preparation of compounds of the invention in case where the compounds of the general formula (I) are monobromosteroids of the general formula (Id):

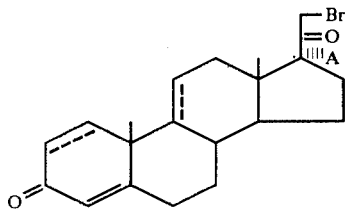

wherein the dotted lines and A are as defined in the general formula (I).

The monobromosteroids of the general formula (Id) can be obtained by racting the dibromosteroids of the general formula (Ic):

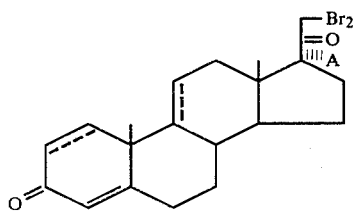

wherein the dotted lines and A are as defined in the general formula (I), with a phosphite such as trialkyl phosphites or triaryl phosphites. The reaction of these dibromosteroids with trialkyl phosphite compounds such as trimethyl phosphite and triethyl phosphite or triaryl phosphite compounds such as triphenyl phosphite gives the monobromosteroids of the general formula (Id) in high yield.

The amount of the phosphite compounds is equimolar to or greater than the dibromosteroid, and preferably 1.2 to 10 times by mole as great as the dibromosteroid.

The reaction ordinarily requires the use of a solvent. The solvents for this purpose may be any solvents which are ordinarily employed industrially. Preferred solvents include nitro compounds such as nitromethane, nitrobenzene and the like, lower alcohols such as methanol, ethanol and the like, lower carboxylic acids such as acetic acid, propionic acid and the like. Especially when lower alcohols or lower carboxylic acids soluble in water are employed, products are caused to precipitate merely by the addition of water to the reaction solution and thus monobromosteroids can be obtained by a simple operation such as filtration.

The reaction temperature is in the range of 0° to 50° C., preferably 5° to 30° C.

As the monobromosteroids of the general formula (Id) there can be mentioned, for example, 21-bromo-17α-hydroxypregn-4-ene-3,20-dione 17-acetate, 21-bromo-17α-hydroxypregn-4-ene-3,20-dione 17-propionate, 21-bromo-17α-hydroxypregna-1,4-diene-3,20-dione 17-acetate, 21-bromo-17α-hydroxypregna-4,9(11)-diene-3,20-dione 17-acetate and the like.

The acyloxysteroids of the formulae (Ia), (Ib), (Ic) and (Id) can be converted into hydrocortisone and prednisolone through the procedure exemplified by the following reaction schema.

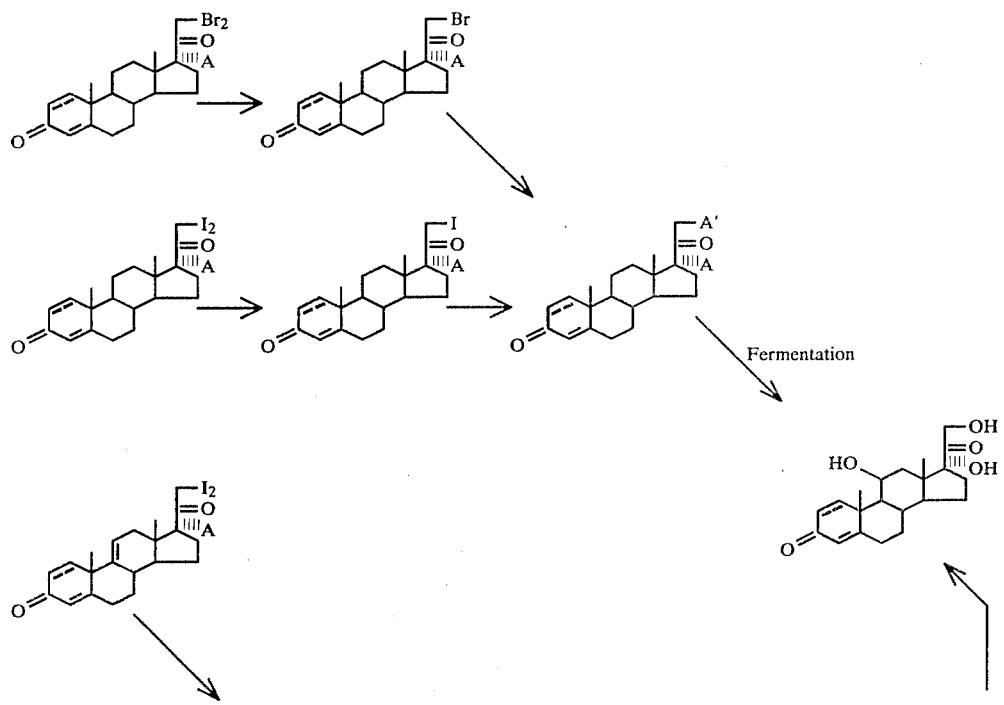

-continued

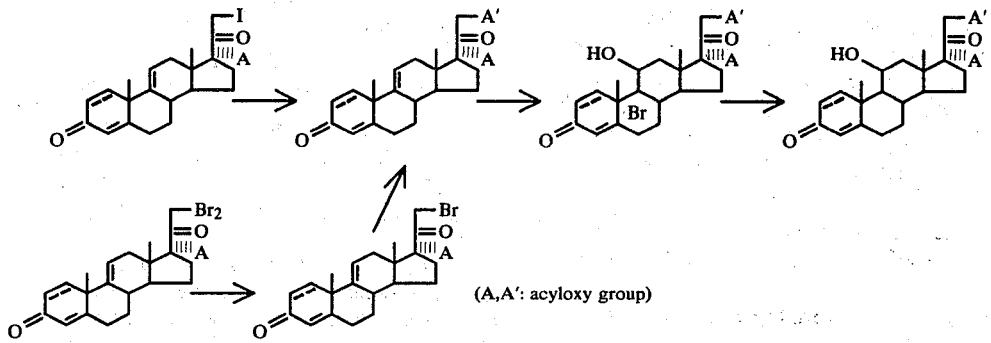

(A,A': acyloxy group)

The processes for preparing various steroids using as a starting material the acyloxysteroids of the general formula (I) according to the present invention will be described.

(i) Preparation of a steroid of the general formula (IV):

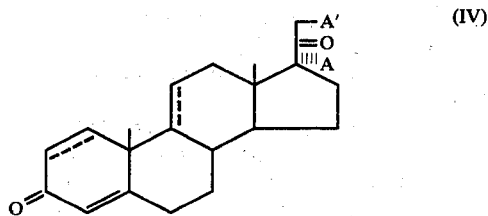

(IV)

wherein the dotted lines represent a single or double bond, and A and A' represent an acyloxy group, from the acyloxysteroid of the general formula (Ib) or (Id)

(a) Process of reacting the acyloxysteroids of the general formula (Ib) or (Id) with quaternary ammonium salts of lower aliphatic acids The quaternary ammonium salts of lower aliphatic acids are quaternary ammonium salts of aliphatic acids having not more than 10 carbon atoms including tetramethylammonium acetate, tetramethylammonium propionate, tetraethylammonium acetate, trimethylbenzylammonium acetate and the like. The amount is equimolar with or greater than that of the steroid (Ib) or (Id) and is preferably in the range of 1.05 to 1.6 times by mole as great as the steroid. For the reaction between the acyloxysteroid of the general formula (Ib) or (Id) and the quaternary ammonium salt of the lower aliphatic acid, there is usually used a solvent. The solvents are preferably aprotic solvents including, for example, dimethylformamide, N-methylpyrolidone, dimethylacetamide and the like.

The reaction temperature is in the range of −10° to 80° C., preferably 0° to 40° C. Higher temperatures are unfavorable because olefinic side products whose acyloxy group at the 17-position is eliminated increase in amounts.

(b) Process of reacting the acyloxysteroids of the general formula (Ib) or (Id) with alkali metal salts of aliphatic acids in the presence of polar, aprotic solvents and/or polyethylene glycols As one of the solvents used in this process is a polar, aprotic solvent such as dimethylsulfoxide, dimethylformamide, dimethylacetamide, N-methylpyrrolidone or the like. When these solvents are used, the halogen atom is substituted with an acyloxy group. The reaction temperature is in the range of 100° C. or below and favorably in the range of 40° to 80° C. Higher temperatures are unfavorable since there are secondarily produced 21-acyloxypregn-4,16-ene-2,20-diones in which the acyloxy group at the 17-position is eliminated, e.g. 21-acetoxypregna-4,16-diene-3,20-dione, 21-acetoxypregna-1,4,16-triene-3,20-dione and the like. Because of conversion of intended 17-acyloxyaceto-17-acyloxysteroids of the general formula (IV) into the above-mentioned side products, too long reaction times are unfavorable. The reaction is generally stopped when the conversion of the starting materials reaches 80 to 97%, preferably 85 to 95%. N-methylpyrrolidone or dimethylacetamide is preferably used since high conversions are attained with reduced formation of side products.

Another solvent or medium includes polyethylene glycols, which are those having a molecular weight of 200 to 1500, preferably 300 to 600 and including polyethylene glycol, polyethylene glycol monomethyl ether, polyethylene glycol dimethyl ether and the like. Some of these polyethylene glycols may be solid, in which case they are used by mixing with a suitable solvent such as, for example, N-methylpyrrolidone, dimethylacetamide, dimethylformamide or the like. Even though the steroids are not dissolved in these polyethylene glycols, the glycols may be used by mixing with a suitable solvent for the steroids. The reaction temperature is generally in the range of 10° to 80° C., preferably 20° to 50° C.

The alkali metal salts of lower aliphatic acids are those which have not more than 10 carbon atoms and include, for example, sodium formate, potassium formate, sodium acetate, potassium acetate, potassium propionate and the like, among which potassium acetate is most preferable.

(c) Reaction of acyloxysteroids of the general formula (Ib) or (Id) with alkali metal salts of lower aliphatic acids in the presence of crown ethers The alkali metal salts of lower aliphatic acids are those defined in (b).

The crown ethers are, for example, macro ring compounds such as 18-crown-6, dibenzo-18-crown-6, dicyclohexyl-18-crown-6, cyclohexyl-12-crown-4, dibenzo-14-crown-4, tetrabenzo-24-crown-8 and the like. Choice of the crown ethers depends on the type of the alkali metal salts: 18-crown-6-compounds are favorable for potassium salts such as potassium acetate, potassium propionate and the like; and cyclohexyl-15-crown-5 and dibenzo-18-crown-6 compounds are favorable for sodium salts such as sodium acetate, sodium propionate and the like. The most preferable combination is a combination of potassium acetate and 18-crown-6. These crown ethers are used in an amount equimolar with or greater than a steroid used and preferably in the range of 1.2 to 2.0 times by mole as great as the steroid.

The reaction usually requires use of solvents. A variety of aprotic solvents may be used and preferably highly polar, aprotic solvents are used such as dimethylformamide, N-methylpyrrolidone, dimethylacetamide and the like. The reaction temperature is generally in the range of 0° to 80° C., preferably 10° to 40° C.

Higher temperatures result in formation of olefinic side products in which the acyloxy group at the 17-position is eliminated.

(ii) Preparation of 17α-hydroxyprogesterone widely used as a drug such as gestagen from the acyloxysteroids of the general formula (Ia) or (Ib)

The contact of the iodosteroids of the general formula (Ia) or (Ib) with methyl ketones can yield progesterones of the general (V):

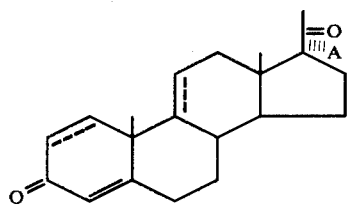

(V)

wherein the dotted lines and A are as defined in the general formula (I).

The methyl ketones used for this purpose include acetone, methyl ethyl ketone, acetophenone and the like, among which acetone is favorably used. These methyl ketones are used in amounts enough for solvent and is preferably employed also as a solvent.

In order to carry out this process, the iodosteroids of the general formula (Ia) or (Ib) are dissolved in, for example, a methyl ketone such as acetone, followed by agitating over a certain time. Where the iodosteroid is a diiodosteroid (Ia) such as 21,21-diiodo-17α-hydroxypregn-4-ene-3,20-dione 17-acetate, a monoiodosteroid such as 21-iodo-17α-hydroxypregn-4-ene-3,20-dione 17-acetate is first produced and further agitation results in formation of 17α-hydroxypregn-4-ene-3,20-dione 17-acetate.

In this process, coexistence of acidic compounds will cause the reaction to proceed much more rapidly with an improved yield of progesterones.

The acidic compounds include, for example, inorganic acids such as hydrochloric acid, hydrobromic acid, perchloric acid and the like, organic acids such as methanesulfonic acid, p-toluenesulfonic acid, trifluoroacetic acid, trifluoromethanesulfonic acid and the like. These acidic compounds may be in the form of salts with weakly basic compounds such as pyridine. These acidic compounds or their salts are ordinarily used in an amount equimolar with the starting iodosteroids. In general, the reaction is effected at temperatures of 0° to 100° C., preferably 10° to 40° C.

The following references and examples are given to further illustrate the present invention and it is to be understood that they are not intended to restrict the invention in any way.

Reference 1:
17β-ethynyl-17α-hydroxyandrosta-1,4-dien-3-one (Synthesis of Starting Material)
17α-ethynyl-17β-nitroxyandrosta-1,4-dien-3-one To 8.0 g of 17α-ethynyl-17β-hydroxyandrosta-1,4-dien-3-one was added 64 ml of acetic anhydride, which was then cooled to −20° C., into which was dropped 6.4 ml of fuming nitric acid, followed by agitating at −20° C. for 1 hour.

The reaction product was poured into 500 g of ice water and agitated. The resulting crystals were filtered and was dissolved in ethyl acetate. The ethyl acetate solution was washed with water, dried and condensed to obtain 8.97 to 17α-ethynyl-17β-nitroxyandrosta-1,4-dien-3-one. This substance could be used as a starting material for use in a subsequent hydrolysis step without purification.

(Hydrolysis)

To 25.0 g of 17α-ethynyl-17β-nitroxyandrosta-1,4-dien-3-one were added 170 ml of tetrahydrofuran, 30 ml of water and 2.0 g of cuprous chloride, followed by agitating under nitrogen atmosphere at 65° C. for 1.5 hours.

After completion of the reaction, 200 ml of benzene and 200 ml of saturated saline solution were added to the reaction solution for extraction of the reaction product. The organic phase was separated, washed twice with saturated saline solution and dried by addition of anhydrous sodium sulfate.

To the crystals obtained by distilling off the solvent were added 250 ml of dichloromethane and 250 ml of n-hexane for recrystallization thereby obtaining 12.69 g of 17β-ethyl-17α-hydroxyandrosta-1,4,-dien-3-one.

The above crystals were further recrystallized from a mixed solvent of benzene and tetrahydrofuran and then from ethyl acetate to obtain pure 17β-ethynyl-17α-hydroxyandrosta-1,4-dien-3-one.

Melting point: 218°–219° C.

Specific rotation: $[\alpha]_D^{24} = +90.9°$; (C: 1.02, tetrahydrofuran).

Mass spectrum: 310 (M+).

NMR spectrum: ((CD₃)₂SO solvent); H of 18-methyl group, δ0.91 ppm (3H, S); H of 19-methyl group, δ1.21 ppm (3H, S); H of ethynyl group, δ2.43 ppm (1H, S).

Reference 2:
17β-ethynyl-17α-hydroxyandrosta-1,4-dien-3-one 17-acetate

To 12.0 g of 17β-ethynyl-17α-hydroxyandrosta-1,4-dien-3-one were added 50 ml of pyridine and 50 ml of acetic anhydride, followed by heating at 120° C. for 30 hours. The reaction product was poured into ice water and the separated tar-like substance was extracted with dichloromethane. The organic phase was washed first with 5% aqueous hydrochloric acid and then 5% aqueous sodium hydrogencarbonate. The separated organic phase was dried over anhydrous sodium sulfate and then concentrated. The concentrate was charged into a column packed with 250 g of alumina and eluted with 500 ml of a mixed solvent of benzene-ethyl acetate (9:1) thereby obtaining 12.3 g of crystals. Upon recrystallization from octane-tetrahydrofuran (20:1), heptane-ethanol (5:1) and octane-tetrahydrofuran (30:7), 8.1 g of 17β-ethynyl-17α-hydroxyandrosta-1,4-dien-3-one 17-acetate. Melting point 171.8°–172.6° C. (temperature increasing rate 1° C./min).

NMR spectrum (CDCl$_3$): δppm: 1.00 (s, 3H), 1.26 (s, 3H); 2.02 (s, 3H), 2.56 (s, 1H); 6.04 (s, 1H), 6.15 (q, 1H); 6.98 (d, 1H).

EXAMPLE 1

To 162 ml of acetic acid and 18 ml of water were added 4.08 g of iodine and 5.71 g of 17β-ethynyl-17α-hydroxyandrosta-1,4-dien-3-one 17-acetate, which was agitated at room temperature. Thereafter, a mixture of 2.6 ml of 40% peracetic acid, 45 ml of acetic acid and 5 ml of water was dropped while agitating and after completion of the dropping, the agitation was further continued for 2.5 hours.

Upon addition of 1500 ml of water, crystals precipitated. The crystals were separated by filtration, washed with water and dried to obtain 9.61 g of 21,21-diiodo-17α-hydroxypregna-1,4-diene-3,20-dione 17-acetate.

NMR spectrum (CDCl$_3$): δppm: 0.89 (s, 3H, 1.24 (s, 3H); 2.09 (s, 3H), 5.52 (s, 1H); 6.11 (s, 1H), 6.31 (q, 1H); 7.10 (d, 1H).

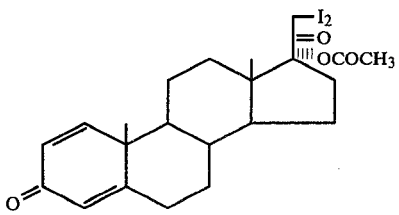

EXAMPLE 2

To 1.04 g of 21,21-diiodo-17α-hydroxypregna-1,4-diene-3,20-dione 17-acetate were added 25 ml of acetone, 4.1 ml of triethylamine and 2.6 ml of acetic acid, followed by agitating at room temperature (25° C.) for 2 hours.

Methylene chloride was added so as to extract the reaction product therewith and the organic phase was sufficiently washed with water. Removal of the methylene chloride by distillation yielded 0.818 g of amorphous crystals.

The liquid chromatographic analysis revealed that they contained 95.3% of 21-iodo-17α-hydroxypregna-1,4-diene-3,20-dione 17-acetate. (Yield 94%).

The recrystallization of the amorphous crystals from acetone-heptane yielded 21-iodo-17α-hydroxypregna-1,4-diene-3,20-dione 17-acetate.

NMR spectrum (CDCl$_3$): δppm: 0.79 (s, 3H), 1.26 (s, 3H); 2.14 (s, 3H), 3.93 (d, 2H); 6.12 (s, 1H), 6.25 (q, 1H); 7.09 (d, 1H).

EXAMPLE 3

To 0.100 g of 21,21-diiodo-17α-hydroxypregna-1,4-diene-3,20-dione 17-acetate was added 1.5 ml of acetone, followed by agitating at 28° C. for 4 hours. The resulting reaction product was extracted with methylene chloride and subjected to the liquid chromatography. As a result, it was found that 21-iodo-17α-hydroxypregna-1,4-diene-3,20-dione 17-acetate was obtained (yield 83.5%) with 11.4% of 17α-hydroxypregna-1,4-diene-3,20-dione 17-acetate as the side product.

EXAMPLE 4

Example 3 was repeated using triethylamine (4.0 ml) instead of acetone as the solvent, thereby obtaining 21-iodo-17α-hydroxypregna-1,4-diene-3,20-dione 17-acetate (yield 40.7%).

EXAMPLE 5

Example 3 was repeated using tetrahydrofuran (4.0 ml) instead of acetone as the solvent, thereby obtaining 21-iodo-17α-hydroxypregna-1,4-diene-3,20-dione 17-acetate (yield 33.5%).

EXAMPLE 6

To 1.00 g of 21,21-diiodo-17α-hydroxypregna-1,4-diene-3,20-dione 17-acetate were added 15 ml of acetone and 70 mg of sodium hydroxide, followed by agitating at 28° C. for 10 minutes and after-treating and analyzing in the same manner as in Example 2 to obtain 21-iodo-17α-hydroxypregna-1,4-diene-3,20-dione 17-acetate (87.8% and 17α-hydroxypregna-1,4-diene-3,20-dione 17acetate (12.2%).

EXAMPLE 7

Example 6 was repeated using, instead of sodium hydroxide, triethylamine (4.2 ml), followed by agitating for 30 minutes, thereby obtaining 21-iodo-17α-hydroxypregna-1,4-diene-3,20-dione 17-acetate (98.5%).

EXAMPLE 8

Into a mixture of 2.016 g of 17β-ethynyl-17α-hydroxyandrosta-1,4-dien-3-one 17-acetate, 1.49 g of iodine, 27 ml of acetic acid, 3 ml of water and 5 ml of benzene was added a mixture of 0.93 ml of 40% peracetic acid, 19.5 ml of acetic acid and 2.2 ml of water, followed by agitating at room temperature for 2.5 hours.

Part of 21,21-diiodo-17α-hydroxypregna-1,4-diene-3,20-dione 17-acetate precipitated as crystals. Then, 6.1 ml of 4.25 wt% sodium hydrogensulfite aqueous solution was dropped while agitating. After completion of the dropping, the agitation was continued for further 3 hours.

The reaction solution was poured into water and extracted with dichloromethane. The dichloromethane phase was washed first with a diluted sodium bicarbonate aqueous solution and then with water. After drying, the dichloromethane solution was analyzed with the liquid chromatography, revealing that there was produced 91.5 mole % of 21-iodo-17α-hydroxypregna-1,4-diene-3,20-dione 17-acetate and 2.2 mole % of 17α-hydroxypregna-1,4-diene-3,20-dione 17-acetate.

The chloroform solution was concentrated and evaporated to dryness under reduced pressure to obtain an oily substance which was gradually solidified. The recrystallization from a mixed solvent of acetone-heptane gave 21-iodo-17α-hydroxypregna-1,4-diene-3,20-dione 17-acetate.

NMR spectrum (CDCl$_3$): δppm: 0.79 (s, 3H, 1.26 (s, 3H); 2.14 (s, 3H), 3.93 (d, 2H); 6.12 (s, 1H), 6.25 (q, 1H); 7.09 (d, 1H).

EXAMPLE 9

A mixture of 7.86 g of 17β-ethynyl-17α-hydroxyandrosta-1,4-dien-3-one 17-acetate, 130 ml of acetic acid, 13 ml of water and 7.35 g of sodium acetate was cooled to 0° C.

6.43 g of N-bromoacetamide was added portion by portion and after completion of the addition, the system was agitated for 1.0 hour. The reaction product was poured into 3 liters of ice water and the resulting crystals were separated by filtration. After drying, 11.58 g of 21,21-dibromo-17α-hydroxypregna-1,4-diene-3,20-dione 17-acetate was obtained.

NMR spectrum (CDCl$_3$): δppm: 0.98 (s, 3H), 1.25 (s, 3H); 2.08 (s, 3H), 6.01 (s, 1H); 6.04 (s, 1H), 6.20 (q, 1H); 7.02 (d, 1H).

MS spectrum: Parent peak: m/e 528.

EXAMPLE 10

A mixture of 100 ml of acetic acid, 10 ml of water, and 2 g of sodium acetate was cooled to 0° C., to which was added 2.0 g of 17β-ethynyl-17α-hydroxyandrost-4-en-3-one 17-acetate.

1.7 g of N-bromoacetamide was added and then agitation was continued for 2 hours. The reaction solution was poured into 500 ml of ice water and the resulting crystals were filtered off and dried to obtain 2.9 g of 21,21-dibromo-17α-hydroxypregn-4-ene-3,20-dione 17-acetate.

To 0.22 g of 21,21-dibromo-17α-hydroxypregn-4-ene-3,20-dione 17-acetate were added 5.0 ml of acetic acid, 0.5 ml of water, 0.1 g of sodium acetate and 0.1 g of zinc powder, followed by agitating at 80° C. for 15 minutes. The zinc powder was filtered off and the filtrate was poured into water to obtain 0.114 g of crystals. Recrystallization from ethanol gave 0.063 g of white crystals. This substance coincided with a reference product of 17α-hydroxyprogesterone 17-acetate with respect to the infrared absorption spectra and the NMR spectra.

EXAMPLE 11

To 1.34 g of 21,21-dibromo-17α-hydroxypregna-1,4-diene-3,20-dione 17-acetate were added 25 ml of nitromethane and 2.0 ml of trimethyl phosphite, followed by agitating at room temperature for 50 minutes. The reaction solution was diluted with ether and washed with water until the aqueous phase was made neutral.

The ether phase was dried and then concentrated and subjected to the removal of the solvents under reduced pressure to obtain 1.117 g of crystals. Crystallization from octane-tetrahydrofuran gave 0.827 g of 21-bromo-17α-hydroxypregna-1,4-diene-3,20-dione 17-acetate.

NMR spectrum (CDCl$_3$): δppm: 0.8 (s, 3H), 1.28 (s, 3H); 2.10 (s, 3H), 3.87 (s, 1H); 3.89 (s, 1H), 6.07 (s, 1H); 6.22 (d, 1H), 7.05 (d, 1H).

MS spectrum: parent peak m/e 448.45.

Elementary analysis: Found (%): C: 61.59, H: 6.61, O: 14.03, Br: 17.78. Calcd.(%): C: 61.47, H: 6.50, O: 14.25, Br: 17.78.

EXAMPLE 12

To 2.03 g of 21,21-dibromo-17α-hydroxypregna-1,4-diene-3,20-dione 17-acetate were added 20 ml of methanol and 2.2 ml of trimethyl phosphite, followed by agitating at room temperature for 80 minutes.

To the reaction solution was added 200 ml of water and the resulting crystals were separated by filtration and dried to obtain 1.69 g of 21-bromo-17α-hydroxypregna-1,4-diene-3,20-dione 17-acetate.

EXAMPLE 13

To 2.07 g of 21,21-dibromo-17α-hydroxypregn-4-ene-3,20-dione 17-acetate were added 20 ml of acetic acid and 2.2 ml of trimethyl phosphite, followed by agitating at room temperature for 70 minutes.

To the reaction solution was added 200 ml of water and the resulting crystals were separated by filtration and dried to obtain 1.63 g of 21-bromo-17α-hydroxypregn-4-ene-3,20-dione 17-acetate.

REFERENCE 3

To a mixture of 2.006 g of 17α-hydroxy-21-iodopregna-1,4-diene-3,20-dione 17-acetate and 0.801 g of tetramethylammonium acetate was added 6.0 ml of N-methylpyrrolidone, followed by agitating at 21° C. for 8 hours. Thereafter, 60 ml of water was slowly dropped while agitating. The resulting crystals were separated by filtration, washed with water and dried to obtain 1.64 g of crystals. Recrystallization from 16 ml of ethanol yielded 1.21 g of 17α,21-dihydroxypregna-1,4-diene-3,20-dione 17,21-diacetate.

NMR spectrum: (CDCl$_3$): δppm: 0.80 (s, 3H), 1.06 (s, 3H); 2.12 (s, 3H), 2.22 (s, 3H); 4.82 (q, 2H), 6.12 (s, 1H); 6.08 (d, 1H), 7.13 (d, 1H).

REFERENCE 4

A mixture of 1.93 g of 17α-hydroxy-21-bromopregna-1,4-diene-3,20-dione 17-acetate, 2.51 g of potassium acetate and 20 ml of dimethylformamide was agitated at 60° C. for 14 hours. Addition of 200 ml of water resulted in precipitation of crystals. When filtered and dried, 1.51 g of crystals were obtained. Recrystallization twice from octane-tetrahydrofuran gave 0.835 g of 17α,21-dihydroxypregna-1,4-diene-3,20-dione 17,21-diacetate.

REFERENCE 5

A mixture of 4.08 g of 17α-hydroxy-21-iodopregna-1,4-diene-3,20-dione 17-acetate, 4.55 g of potassium acetate, 28 ml of polyethylene glycol monomethyl ether (molecular weight: 400), and 12 ml of N-methylpyrrolidone was agitated at 40° C. for 13 hours. The reaction solution was dropped into 400 ml of water. The resulting crystals were filtered and dried to obtain 3.29 g of crude 17α,21-dihydroxypregna-1,4-diene-3,20-dione 17,21-diacetate. The analysis of the liquid chromatography revealed that the purity was 70.13%.

REFERENCE 6

A mixture of 1.86 g of 17α-hydroxy-21-iodopregna-1,4-diene-3,20-dione 17-acetate, 2.00 g of potassium acetate, 1.952 g of 18-crown-6 and 20 ml of N-methylpyrrolidone was agitated at 20° C. for 4 hours. The reaction solution was poured into 200 ml of water and the resulting crystals were filtered off and dried to obtain 1.33 g of crude 17α,21-dihydroxypregna-1,4-diene-3,20-dione 17,21-diacetate. The analysis of the liquid chromatography releaved that the purity was 90% (yield: 74.5 mole %).

Recrystallization from ethanol gave pure 17α,21-dihydroxypregna-1,4-diene-3,20-dione 17,21-diacetate.

REFERENCE 7

To 1.0 g of 21,21-diiodo-17α-hydroxypregna-1,4-diene-3,20-dione 17-acetate was added 15 ml of acetone, followed by agitating at 28° C. for 4 hours. The reaction product was extracted with methylene chloride and the methylene chloride phase was washed with water and then dried. The solvent was distilled off and evaporated to dryness to obtain amorphous crystals.

The analysis of the liquid chromatography demonstrated that the crystals were made of a mixture of 21-iodo-17α-hydroxypregna-1,4-diene-3,20-dione 17-acetate (83.5%) and 17α-hydroxypregna-1,4-diene-3,20-dione 17-acetate (11.4%). When the reaction was continued for 21 hours, there was obtained a mixture of 21-iodo-17α-hydroxypregna-1,4-diene-3,20-dione 17-acetate (46.0%) and 17α-hydroxypregna-1,4-diene-3,20-dione 17-acetate (48.3%). The continuation over 50 hours resulted in formation of 17α-hydroxypregna-1,4-diene-3,20-dione 17-acetate in a yield of 80%.

REFERENCE 8

To 1.0 g of 21-iodo-17α-hydroxypregna-1,4-diene-3,20-dione 17-acetate were added 20 ml of acetone and 0.80 g of pyridine p-toluenesulfonate, followed by heating for 2.5 hours under refluxing and agitating conditions. As a result, 17α-hydroxypregna-1,4-diene-3,20-dione 17-acetate was obtained in a yield of 98%.

Then, the after-treatment was carried out in the same manner as in Reference 7 to obtain white crystals. Recrystallization from heptane-acetone gave 17α-hydroxypregna-1,4-diene-3,20-dione 17-acetate.

NMR spectrum: (CDCl₃): δppm: 0.71 (s, 3H), 1.25 (s, 3H); 2.02 (s, 3H), 2.06 (s, 3H); 6.03 (s, 1H), 6.32 (q, 1H); 7.01 (d, 2H).

Having now fully described the invention, it will be apparent to one of ordinary skill in the art that many changes and modifications can be made thereto without departing from the spirit of the invention as set forth herein.

What is claimed is:

1. A diiodosteroid of formula (Ia):

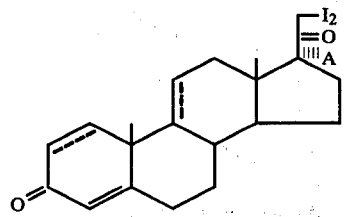

(Ia)

wherein the dotted lines in the rings independently represent a single or double bond and A represents an acyloxy group.

2. A process for producing a diiodosteroid of formula (Ia):

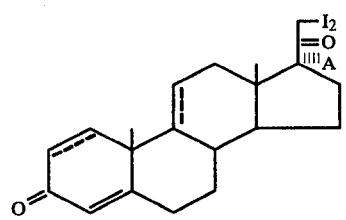

(Ia)

wherein the dotted lines in the rings independently represent a single or double bond and A represents an acyloxy group, which comprises: reacting an iodizing agent selected from the group consisting of N-iodoimide, N-iodoamide and the combination of an oxidizing agent and iodine capable of releasing positive iodine atoms with a 17β-ethynyl-17α-acyloxysteroid of formula (II):

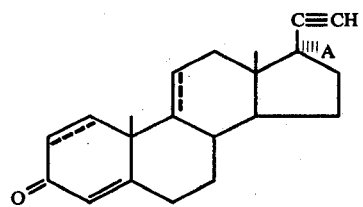

(II)

wherein the dotted lines and A are as defined in formula (Ia).

3. The process of claim 2, wherein said iodizing agent is an N-iodoimide or an N-iodoamide.

4. The process of claim 2, wherein said iodizing agent comprises an oxidizing agent and iodine.

5. A process for producing a monoiodosteroid of formula (Ib):

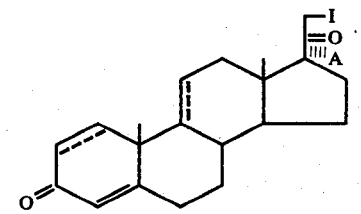

(Ib)

wherein the dotted lines in the rings independently represent a single or double bond and A represents an acyloxy group, which comprises: contacting a diiodosteroid of formula (Ia):

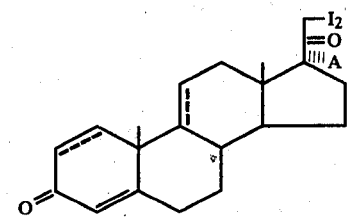

(Ia)

wherein the dotted lines and A are as defined in formula (Ib), with an organic solvent selected from the group consisting of methyl ketones and amines.

6. The process of claim 5, wherein said diiodosteroid is contacted in said organic solvent with a base.

7. The process for producing a monoiodosteroid of formula (Ib):

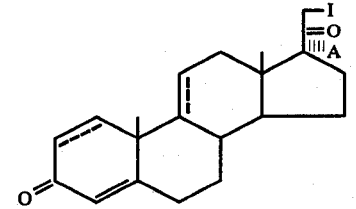

(Ib)

wherein the dotted lines in the rings independently represent a single or double bond and A represents an acyloxy group, which comprises: reducing a diiodosteroid of formula (Ia):

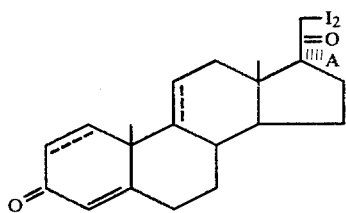 (Ia)

wherein the dotted line and A are as defined in formula (Ib), with a dithionite.

8. A dibromosteroid of formula (Ic):

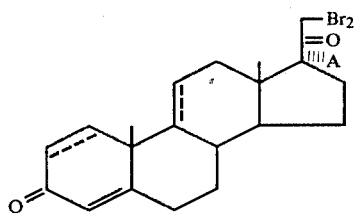 (Ic)

wherein the dotted lines in the rings independently represent a single or double bond and A represents an acyloxy group.

9. A process for producing a dibromosteroid of formula (Ic):

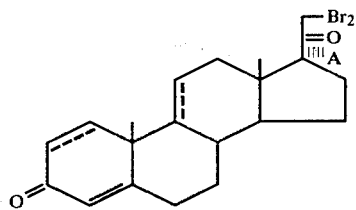 (Ic)

wherein the dotted lines in the rings independently represent a single or double bond and A represents an acyloxy group, which comprises: reacting N-bromoimide or N-bromoamide with a 17β-ethynyl-17α-acyloxysteroid of formula (II):

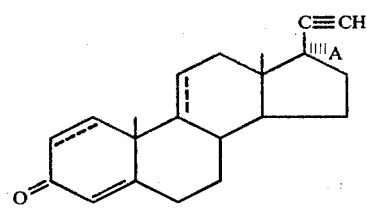 (II)

wherein the dotted lines and A are as defined in formula (Ic).

10. A process for producing a monobromosteroid of formula (Id):

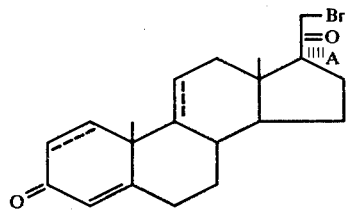 (Id)

wherein the dotted lines in the rings independently represent a single or double bond and A represents an acyloxy group, which comprises: reacting a dibromosteroid of formula (Ic):

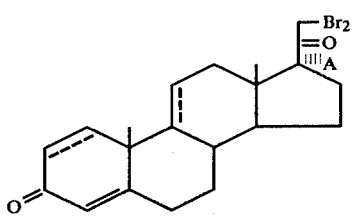 (Ic)

wherein the dotted lines and A are as defined in formula (Id), with a trialkyl phosphite or a triaryl phosphite.

* * * * *